(12) United States Patent
Charbit

(10) Patent No.: US 9,265,704 B2
(45) Date of Patent: Feb. 23, 2016

(54) COSMETIC COMPOSITION COMPRISING A CUCURBIC ACID COMPOUND AND AN ACRYLIC COPOLYMER

(75) Inventor: Yael Charbit, Vitry sur Seine (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/995,704

(22) PCT Filed: Dec. 15, 2011

(86) PCT No.: PCT/EP2011/072979
§ 371 (c)(1),
(2), (4) Date: Aug. 14, 2013

(87) PCT Pub. No.: WO2012/084699
PCT Pub. Date: Jun. 28, 2012

(65) Prior Publication Data
US 2013/0315853 A1    Nov. 28, 2013

Related U.S. Application Data

(60) Provisional application No. 61/427,234, filed on Dec. 27, 2010.

(30) Foreign Application Priority Data

Dec. 20, 2010    (FR) ..................... 10 60817

(51) Int. Cl.
| A61K 8/365 | (2006.01) |
| A61Q 19/00 | (2006.01) |
| A61Q 5/00 | (2006.01) |
| A61K 8/81 | (2006.01) |

(52) U.S. Cl.
CPC . *A61K 8/365* (2013.01); *A61K 8/81* (2013.01); *A61K 8/8158* (2013.01); *A61Q 5/00* (2013.01); *A61Q 19/00* (2013.01); A61K 2800/48 (2013.01)

(58) Field of Classification Search
CPC . A61K 8/365; A61K 8/8158; A61K 2800/48; A61K 8/81; A61Q 5/00; A61Q 19/00
See application file for complete search history.

(56) References Cited

U.S. PATENT DOCUMENTS

2004/0029839 A1 * 2/2004 Boulle et al. .................. 514/129

FOREIGN PATENT DOCUMENTS

| DE | 102007029735 A1 | 1/2009 |
| EP | 1333021 A2 | 8/2003 |
| EP | 2345402 A1 | 7/2011 |
| JP | 2003-238388 A | 8/2003 |
| JP | 2003-300856 A | 10/2003 |
| JP | 2006-008796 A | 1/2006 |

OTHER PUBLICATIONS

Anonymous: "Simugel™ NS, An emulsifying/thickening polymer for New Sensations", Internet Citation—URL:http://www.seppic.com, Jul. 2001, XP002256259.
Japanese Office Action issued Aug. 3, 2015 in JP Appln No. 2013-545213.
Anonymous: "Simugel™ NS, An emulsifying/thickening polymer for New Sensations", Internet Citation—URL:http://www.seppic.com, Jul. 2001, XP002256259,.
Gottschalck et al., "International Cosmetic Ingredient Dictionary and Handbook, Passage", Jan. 1, 2008, International Cosmetic Ingredient Dictionary and Handbook, the Cosmetic, Toiletry, and Fragrance Association, Washington, DC, p. 1248, XP002580204.
Japanese Office Action issued Aug. 3, 2015 in JP Appin No. 2013-545213.

* cited by examiner

*Primary Examiner* — Ali Soroush
*Assistant Examiner* — Genevieve S Alley
(74) *Attorney, Agent, or Firm* — Novak Druce Connolly Bove + Quigg LLP

(57) ABSTRACT

The invention relates to a cosmetic composition comprising, in a physiologically acceptable aqueous medium, a cucurbic acid compound of formula (I) in which $R_1$ represents a radical $COOR_3$, where $R_3$ denotes H or a $C_1$-$C_4$ alkyl radical, which is optionally substituted by one or more hydroxyl groups; $R_2$ represents a hydrocarbon radical having from 1 to 18 carbon atoms; and a copolymer of 2-acrylamido-2-methylpropane-sulphonic acid and hydroxylated $C_2$-$C_4$ alkyl(meth)acrylate. Application to the care and make-up of keratin materials.

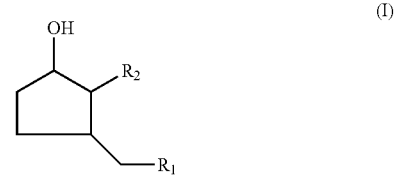

(I)

20 Claims, No Drawings

COSMETIC COMPOSITION COMPRISING A CUCURBIC ACID COMPOUND AND AN ACRYLIC COPOLYMER

CROSS REFERENCE TO RELATED APPLICATIONS

This application is a National Phase filing under 35 U.S.C. §371 of PCT/EP2011/072979 filed on Dec. 15, 2011; and this application claims priority to Application No. 1060817 filed in France on Dec. 20, 2010, and this application claims the benefit of U.S. Provisional Application No. 61/427,234 filed on Dec. 27, 2010; the entire contents of all are hereby incorporated by reference.

The present invention relates to compositions, especially cosmetic compositions, comprising a cucurbic acid compound and a 2-acrylamido-2-methylpropanesulphonic acid copolymer, and to the use of these compositions in a method for treating keratin materials of human beings.

More particularly the compositions of the invention are intended for the care and/or make-up of keratin materials.

For the purposes of the invention, "keratin materials" are understood to denote, for example, the skin, the mucous membranes, the lips, the scalp, the eyelashes, the eyebrows and the head hair.

Patent application EP-A-1333021 discloses hydrogenated compounds of cucurbic acid such as 3-hydroxy-2-pentylcyclopentaneacetic acid for promoting desquamation of the skin and for stimulating epidermal renewal, for combating the signs of skin ageing, enhancing the lightness of the complexion and/or smoothing the skin of the face. Patent application FR-A62921255 likewise describes these compounds, for use as depigmenting agents.

The introduction of the aforementioned hydrogenated compounds of cucurbic acid into an aqueous cosmetic formulation, however, may be accompanied by a not insignificant decrease in viscosity, thereby giving rise to substantial fluidification of the composition and, consequently, to its destabilization.

Too fluid a composition is difficult to apply to the keratin materials. A composition of this kind runs from the keratin materials, particularly the skin, to which it is applied. Its application to the keratin materials that are the desired target of the treatment lacks precision, thereby making it fairly unattractive to use.

Moreover, the presence of a hydrogenated compound of cucurbic acid is found to be detrimental to the thickening power of certain conventional gelling agents.

Accordingly, a need exists to have cosmetic compositions comprising a cucurbic acid compound which exhibit high stability over time, especially after storage for 2 months at ambient temperature (25° C.), without substantial fluidification.

The purpose of the present invention is to meet these needs.

More specifically, the present invention relates to a non-foaming composition comprising, in a physiologically acceptable medium including an aqueous medium, at least one cucurbic acid compound of formula (I) and at least one specific 2-acrylamido-2-methylpropanesulphonic acid copolymer, as are described below.

The composition according to the invention is more particularly a cosmetic composition.

Surprisingly, the inventors have observed that the addition of a cucurbic acid compound to a composition comprising a specific 2-acrylamido-2-methylpropane-sulphonic acid copolymer produces a composition which is stable over time, without substantial fluidification.

Further, the composition according to the invention presents good cosmetic properties such as for example, it is less sticky, easily spread (without drag) and bring comfort.

The present invention also relates to a method for non-therapeutic care or make-up treatment of keratin materials, which comprises applying to said keratin materials a composition in accordance with the invention. A method of this kind is intended advantageously for the care or make-up of the skin.

The compound derived from cucurbic acid is a compound selected from those conforming to formula (I) below:

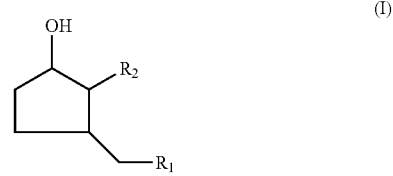

in which:

$R_1$ represents a radical $COOR_3$, where $R_3$ denotes a hydrogen atom or a $C_1$-$C_4$ alkyl radical, which is optionally substituted by one or more hydroxyl groups;

$R_2$ represents a saturated or unsaturated hydrocarbon radical which is linear and has from 1 to 18 carbon atoms or is branched or cyclic and has from 3 to 18 carbon atoms;

and also the optical isomers thereof and corresponding salts.

Preferably $R_1$ denotes a radical selected from —COOH, —COOMe, —COO—$CH_2$—$CH_3$, —COO—$CH_2$—CH(OH)—$CH_2$OH, —COO$CH_2$—$CH_2$—$CH_2$OH, —COO$CH_2$—CH(OH)—$CH_3$.

Preferentially $R_1$ denotes a —COOH radical.

Preferentially $R_2$ denotes a saturated or unsaturated linear hydrocarbon radical which preferably has from 2 to 7 carbon atoms. More particularly $R_2$ may be a pentyl, pentenyl, hexyl or heptyl radical.

According to one embodiment, the compound of formula (I) is selected from 3-hydroxy-2-[(2Z)-2-pentenyl]cyclopentaneacetic acid or 3-hydroxy-2-pentylcyclopentaneacetic acid. Preferably the compound (I) is 3-hydroxy-2-pentylcyclopentaneacetic acid; this compound may in particular be in the form of the sodium salt.

The salts of the compounds which can be used according to the invention are selected more particularly from alkali metal salts, such as sodium and potassium salts; alkaline-earth metal salts, such as calcium, magnesium and strontium salts, and metal salts, such as zinc, aluminium, manganese and copper salts; salts of ammonium of formula $NH_4^+$; quaternary ammonium salts; salts of organic amines, such as methylamine, dimethylamine, trimethylamine, triethylamine, ethylamine, 2-hydroxy-ethylamine, bis(2-hydroxyethyl)amine and tri(2-hydroxyethyl)amine salts; and lysine and arginine salts. Preference is given to using the salts selected from sodium, potassium, magnesium, strontium, copper, manganese and zinc salts. Preferentially the sodium salt is used.

The compound of formula (I) defined above may be present in the composition according to the invention in an amount of from 1% to 10% by weight, relative to the total weight of the composition, preferably from 1.5% to 5% by weight.

The composition according to the invention comprises a copolymer of 2-acrylamido-2-methylpropanesulphonic acid and hydroxylated $C_2$-$C_4$ alkyl(meth)acrylate, which is optionally salified.

The hydroxylated $C_2$-$C_4$ alkyl(meth)acrylate monomer may be selected from 2-hydroxyethyl acrylate, 2-hydroxyethyl methacrylate, 2,3-dihydroxypropyl acrylate and 2,3-dihydroxypropyl methacrylate.

Said copolymer may be salified, particularly in the form of an alkali metal salt such as, for example, the sodium or potassium salt, or in the form of an ammonium salt, or in the form of an amino alcohol salt such as, for example, the monoethanolamine salt, or in the form of an amino acid salt such as, for example, the lysine salt.

Advantageously the copolymer is salified in the form of the sodium salt.

The composition preferably comprises the copolymer of 2-acrylamido-2-methylpropanesulphonic acid and 2-hydroxyethyl acrylate, particularly in the sodium salt form, such as, for example, the copolymers sold under the trade names Sepinov® EMT 10 or Simulgel® NS by SEPPIC (INCI name: Hydroxyethyl acrylate/sodium acryloyldimethyl taurate copolymer).

Polymers of these kinds are described in patent application FR-A-2856691.

The copolymer of 2-acrylamido-2-methylpropanesulphonic acid and hydroxylated $C_2$-$C_4$ alkyl(meth)acrylate may be present in the composition according to the invention in an amount of from 0.1% to 10% by weight, relative to the total weight of the composition. The amount of said copolymer may be preferably from 0.5% to 5% by weight, relative to the total weight of the composition.

Advantageously, the cucurbic acid compound of formula (I) (referred to as A) and the copolymer of 2-acrylamido-2-methylpropanesulphonic acid and hydroxylated $C_2$-$C_4$ alkyl (meth)acrylate (referred to as B) described above may be present in the composition according to the invention in an A/B weight ratio of from 0.5 to 4.

Preferably, this A/B weight ratio may be from 0.5 to 3. Preferentially, this A/B weight ratio may be from 0.5 to 2.5.

The composition according to the invention is a non-foaming composition: it is free from foaming surfactant.

Foaming surfactants are detergents and differ from emulsifiers in their HLB value (hydrophilic/lipophilic balance), the HLB being the ratio between the hydrophilic moiety and the lipophilic moiety in the molecule. The term HLB is well known to the skilled person and is described in, for example, "The HLB system. A time-saving guide to Emulsifier Selection" (published by ICI Americas Inc.; 1984). For emulsifiers, the HLB is generally from 3 to 8 for the preparation of W/O emulsions and from 8 to 18 for the preparation of O/W emulsions, whereas foaming surfactants generally have an HLB of more than 20. Foaming surfactants are described in patent application EP-A-1702609, for example.

The viscosity of a composition of the invention may be measured by any method known to the skilled person, and especially by the following conventional method.

Thus the measurement may be made at 25° C. using a Rheomat 180 equipped with a spindle rotating at 200 rpm. The skilled person is able to select the spindle allowing the viscosity to be measured, from spindles M1 or M2 or M3 or M4, on the basis of his or her general knowledge, such that the measurement can be conducted.

The composition according to the invention comprises a physiologically acceptable aqueous medium.

A "physiologically acceptable medium" denotes a medium which is compatible with the keratin fibres and/or materials of human beings, such as, for example, non-limitatively, the skin, the mucous membranes, the nails, the scalp and/or the head hair.

This physiologically acceptable aqueous medium comprises an aqueous phase, optionally as a mixture or not with one or more organic solvents such as a $C_1$-$C_8$ alcohol, particularly ethanol, isopropanol, tert-butanol, n-butanol, polyols such as glycerol, propylene glycol, butylene glycol, and polyol ethers.

A composition according to the invention may also comprise a fatty phase, which may comprise oils, gums and waxes which are commonly used in the relevant field of application.

Thus, according to one embodiment, a composition according to the invention may further comprise at least one fatty phase selected from a fatty phase which is solid at ambient temperature (20-25° C.) and atmospheric pressure and/or a fatty phase which is liquid at ambient temperature (20-25° C.) and atmospheric pressure.

A liquid fatty phase suitable for the implementation of the invention may comprise a volatile oil, a non-volatile oil, and a mixture thereof. A volatile or non-volatile oil may be a hydrocarbon oil, especially one of animal or plant origin, a synthetic oil, a silicone oil, a fluoro oil or a mixture thereof.

A solid fatty phase suitable for the implementation of the invention may be, for example, selected from pastelike fats, gums and mixtures thereof.

Oils which can be used in the invention include mineral oils (liquid petrolatum), vegetable oils (liquid fraction of shea butter, sunflower oil), synthetic oils (Purcellin oil), silicone oils or waxes (cyclomethicone) and fluoro oils (perfluoropolyethers). These oils may be admixed with fatty alcohols and fatty acids (stearic acid).

When a composition is an emulsion, the proportion of the fatty phase may be from 5% to 80% by weight, and preferably from 5% to 50% by weight, relative to the total weight of the composition. The oils, waxes, emulsifiers and co-emulsifiers used in the composition in emulsion form are selected from those conventionally used in the cosmetics field.

One or more emulsifiers may be present in a composition of the invention in a proportion of from 0.3% to 30% by weight, and more particularly from 0.5% to 20% by weight, relative to the total weight of the composition.

The composition according to the invention may also comprise customary adjuvants within the relevant field, such as emulsifiers, hydrophilic or lipophilic gelling agents, waxes, hydrophilic or lipophilic additives, preservatives, antioxidants, solvents, fragrances, fillers, UVA and/or UVB filters (organic or inorganic, soluble or insoluble), pigments, fibres, chelating agents, odour absorbers, colourants and other active cosmetic ingredients.

The amounts of these various adjuvants are those conventionally used in the cosmetics field, and may vary, for example, from 0.01% to 30% of the total weight of the composition. Generally speaking, the amounts are adjusted in accordance with the formulation produced. These adjuvants, according to their type, may be introduced into the fatty phase, into the aqueous phase and/or into the lipid spherules.

The composition according to the invention may advantageously comprise a 2-acrylamido-2-methylpropanesulphonic acid homopolymer, more particularly in partly or totally neutralized form. A polymer of this kind can reduce the stickiness of the composition when it is applied to the skin.

Preferentially, said homopolymer may be partly or totally neutralized with a mineral base (sodium hydroxide, potassium hydroxide, aqueous ammonia) or an organic base such as mono-, di- or tri-ethanolamine, an aminomethylpropanediol, N-methylglucamine, basic amino acids such as arginine and lysine, and mixtures of these compounds. They are generally neutralized. "Neutralized" in the present invention means polymers which are totally or almost totally neutralized, in other words neutralized to an extent of at least 90%.

The homopolymer may have a number-average molecular weight of from 1000 to 20 000 000 g/mol, preferably of from 20 000 to 5 000 000 and more preferably of from 100 000 to 1 500 000 g/mol.

The homopolymer may be crosslinked, particularly using crosslinking agents which may be selected from the polyolefinically unsaturated compounds commonly used for crosslinking polymers obtained by free-radical polymerization.

Crosslinking agents include, for example, divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl(meth)acrylate, allyl ethers of alcohols from the series of the sugars, or other allyl or vinyl ethers of polyfunctional alcohols, and also the allyl esters of phosphoric and/or vinylphosphonic acid derivatives, or mixtures of these compounds.

According to one preferred embodiment of the invention, the crosslinking agent is selected from methylenebisacrylamide, allyl methacrylate or trimethylolpropane triacrylate (TMPTA). The degree of crosslinking is generally from 0.01 to 10 mol % and more particularly from 0.2 to 2 mol %, relative to the polymer.

Polymers of this type include, in particular, the crosslinked and neutralized 2-acrylamido-2-methylpropanesulphonic acid homopolymer sold by Clariant under the trade name Hostacerin® AMPS (CTFA name: ammonium polyacryldimethyltauramide).

A composition of the invention may take any of the formulation forms it is possible to contemplate.

In particular, a composition according to the invention may have the form of an aqueous or aqueous-alcoholic solution; a dispersion; a water-in-oil, oil-in-water or multiple emulsion; a suspension; microcapsules or microparticles; ionic and/or non-ionic vesicle dispersions; or an aerosol composition further comprising a pressurized propellant. The composition according to the invention may preferentially be an oil-in-water or water-in-oil emulsion. More preferably the composition according to the invention is an oil-in-water emulsion.

When the composition comprises an oily phase, this phase may comprise a silicone elastomer. Examples of silicone elastomers are described in patent application WO-A-2009/080958.

A composition according to the invention may also take the form of a care product, a sun or aftersun product, a care product for everyday protection from light, a product for the body, a foundation for application to the face or neck, a concealer product, a complexion corrector, a tinted cream or a make-up base for make-up for the face, or a make-up composition for the body.

A composition according to the invention may be used for enhancing the general condition of an epidermis, more particularly of the skin, and particularly for maintaining or restoring its physiological functions and/or its aesthetic appearance.

Other features and advantages of the invention will become apparent more clearly from the examples below, which are given illustratively and not limitatively. In the text above and below, the proportions are given as weight percentages unless indicated otherwise.

COMPARATIVE EXAMPLES 1 TO 4

Four compositions (face care cream) were produced, which are described in the table below: two compositions according to the invention (Examples 3 and 4), containing the sodium salt of 3-hydroxy-2-pentylcyclopentaneacetic acid and the sodium 2-acrylamido-2-methylpropanesulphonate/2-hydroxyethyl methacrylate copolymer, and two non-inventive compositions: one without the two compounds (Example 2) and the other without the copolymer (Example 1).

A measurement was then made of the viscosity of the compositions obtained after 24 hours of storage at ambient temperature (viscosity measured at 25° C. using a Rheomat 180 with spindle M3 after 10 minutes of rotation at 200 revolutions/minute). The composition was also centrifuged for 1 hour at 25° C. and at 900 G.

Additionally, the composition was evaluated microscopically.

An evaluation was also made of the stability of each composition after storage for 2 months at ambient temperature (25° C.) and at 45° C.

The results obtained were as follows:

| Example | 1 (non-i) | 2 (non-i) | 3 | 4 |
|---|---|---|---|---|
| Sodium salt of 3-hydroxy-2-pentylcyclopentaneacetic acid, 30% in a water/dipropylene glycol (70/30) mixture | 6.7% or 2% a.i. | — | 6.7% or 2% a.i. | 6.7% or 2% a.i. |
| Water | qs 100 | qs 100 | qs 100 | qs 100 |
| Sodium 2-acrylamido-2-methyl-propanesulphonate/2-hydroxyethyl methacrylate copolymer, 90% in water (Sepinov EMT 10 from SEPPIC) | — | — | 1 | 3 |
| Polyacrylamidomethylpropane-sulphonic acid partly neutralized with aqueous ammonia and highly crosslinked (Hostacerin AMPS ® from Clariant) | 1 | 1 | 1 | 0 |
| Condensate of ethylene oxide and propylene oxide and ethylene oxide (128 EO/54 PO/128 EO) (Synperonic PE/F 108 from Croda) | 0.15 | 0.15 | 0.15 | 0.15 |

-continued

| Example | 1 (non-i) | 2 (non-i) | 3 | 4 |
|---|---|---|---|---|
| Ethoxylated sorbitan monooleate (20 EO) (Tween 80 from Croda) | 0.5 | 0.5 | 0.5 | 0.5 |
| Ethanol | 10 | 10 | 10 | 10 |
| Isopropyl N-lauroylsarcosinate | 1.5 | 1.5 | 1.5 | 1.5 |
| Mixture (13/87) of organopolysiloxane elastomer and cyclohexasiloxane (Gransil RPS-D6 from Grant Industries) | 25 | 25 | 25 | 25 |
| Cetyl dimethicone copolyol (Abil EM 90 from Goldschmidt) | 2 | 2 | 2 | 2 |
| Polytetrafluoroethylene wax (Ceridust 9205 F from Clariant) | 1 | 1 | 1 | 1 |
| Perlite | 0.35 | 0.35 | 0.35 | 0.35 |
| Sodium hydroxide | 0.026 | 0.026 | 0.026 | 0.026 |
| Preservative | qs | qs | qs | qs |
| Viscosity (Pa · s) | <0.6 | 0.7-1.1 | 1 | 1.57 |
| Centrifugation | Triphase | Remains homogeneous | Remains homogeneous | Remains homogeneous |
| Microscopic appearance | Very heterogeneous | Homogeneous | Homogeneous | Homogeneous |
| Stability 2 months at 25° C. and at 45° C. | Unstable | Stable | Stable | Stable | non-i = non-inventive
a.i. = active ingredient

These tests show that the control formula (Example 2) is stable.

The formula containing only the sodium salt of 3-hydroxy-2-pentylcyclopentaneacetic acid (Example 1) is not stable: introducing this active ingredient into the control vehicle destabilizes the composition.

The formula according to the invention (Example 3) containing the sodium salt of 3-hydroxy-2-pentylcyclopentaneacetic acid and the sodium 2-acrylamido-2-methyl-propanesulphonate/2-hydroxyethyl methacrylate copolymer is stable. This copolymer therefore stabilizes the composition containing the acidic active ingredient.

Moreover, the composition of Example 3, which additionally contains the polyacrylamidomethylpropanesulphonic acid partly neutralized with aqueous ammonia and highly crosslinked (Hostacerin AMPS® from Clariant), when applied to the skin, has a less sticky appearance than the composition of Example 4.

COMPARATIVE EXAMPLES 5 to 7

Three compositions (face care cream) were produced, which are described in the table below: one composition according to the invention (Example 7), containing the sodium salt of 3-hydroxy-2-pentylcyclopentaneacetic acid and the sodium 2-acrylamido-2-methylpropanesulphonate/2-hydroxyethyl methacrylate copolymer, and two non-inventive compositions: one without the copolymer (Example 5), and the other without the acidic active ingredient (Example 6).

The viscosity of the compositions was then measured under the same conditions as those described in the example above.

Additionally, the composition was evaluated microscopically.

The results obtained were as follows:

| Example | 5 (non-i) | 6 (non-i) | 7 |
|---|---|---|---|
| Sodium salt of 3-hydroxy-2-pentylcyclopentaneacetic acid, 30% in a water/dipropylene glycol mixture (70/30) | 6.7% or 2% a.i. | 0 | 6.7% or 2% a.i. |
| Water | qs 100 | qs 100 | qs 100 |
| Sodium 2-acrylamido-2-methyl-propanesulphonate/2-hydroxyethyl methacrylate copolymer, 90% in water (Sepinov EMT 10 from SEPPIC) | — | 1 | 1 |
| Acrylic acid/stearyl methacrylate copolymer polymerized in an ethyl acetate/cyclohexane mixture (Pemulen TR-1 Polymer from Noveon) | 0.2 | 0.2 | 0.2 |
| Acrylamide/sodium 2-acrylamido-2-methylpropanesulphonate copolymer in inverse emulsion, 40% in isoparaffin/water (Sepigel 305 from SEPPIC) | 1 | 1 | 1 |

-continued

| Example | 5 (non-i) | 6 (non-i) | 7 |
|---|---|---|---|
| Mixture of glyceryl stearate and PEG-100 stearate (Arlacel ® 165 FL from Uniqema) | 0.75 | 0.75 | 0.75 |
| Mixture of cetylstearyl glucoside and cetyl and stearyl alcohols (12/46/42) (Montanov 68 from SEPPIC) | 2 | 2 | 2 |
| Ethanol | 7 | 7 | 7 |
| Dimethicone 10 cst | 3 | 3 | 3 |
| Polyethylene glycol (20 EO) (Carbowax Sentry Polyethylene Glycol 1000 NF, FCC Grade from Dow Chemical) | 2 | 2 | 2 |
| 2-Ethylhexyl cyano-3,3-diphenyl-acrylate | 7 | 7 | 7 |
| Ethylhexyl salicylate | 5 | 5 | 5 |
| Butyl methoxydibenzoylmethane | 3 | 3 | 3 |
| Perlite | 0.3 | 0.3 | 0.3 |
| Lactic acid | 0.25 | 0.25 | 0.25 |
| Stearyl alcohol | 1 | 1 | 1 |
| Diisopropyl sebacate | 4 | 4 | 4 |
| Shea butter | 1 | 1 | 1 |
| Preservative | qs | qs | qs |
| Viscosity (Pa · s) | <0.5 | 0.65 | 0.86-1.03 |
| Microscopic appearance | Heterogeneous: globular emulsion, untidy edges | Homogeneous | More homogeneous |

The composition of Example 7 according to the invention is stable, whereas the composition of Example 5, which does not contain the sodium 2-acrylamido-2-methyl-propanesulphonate/2-hydroxyethyl methacrylate copolymer, is not stable.

The invention claimed is:

1. A non-foaming composition comprising, in a physiologically acceptable aqueous medium, a compound of formula (I) below:

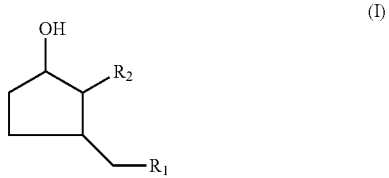

in which:
R$_1$ represents a radical COOR$_3$, where R$_3$ denotes a hydrogen atom or a C$_1$-C$_4$ alkyl radical, which is optionally substituted by one or more hydroxyl groups;
R$_2$ represents a saturated or unsaturated hydrocarbon radical which is linear and has from 1 to 18 carbon atoms or is branched or cyclic and has from 3 to 18 carbon atoms; and also the optical isomers thereof and corresponding salts;
and a copolymer of 2-acrylamido-2-methylpropanesulphonic acid and hydroxylated C$_2$-C$_4$ alkyl(meth)acrylate, which is optionally salified.

2. The composition according to claim 1, wherein the compound (I) is such that R$_1$ denotes a radical selected from —COOH, —COOMe, —COO—CH$_2$—CH$_3$, —COO—CH$_2$—CH(OH)—CH$_2$OH, —COOCH$_2$—CH$_2$—CH$_2$OH, —COOCH$_2$—CH(OH)—CH$_3$; and R$_2$ denotes a saturated or unsaturated linear hydrocarbon radical having from 2 to 6 carbon atoms.

3. The composition according to claim 1, wherein the compound (I) is 3-hydroxy-2-pentylcyclopentaneacetic acid.

4. The composition according to claim 1, wherein the compound of formula (I) is present in an amount of from 1% to 10% by weight, relative to the total weight of the composition.

5. The composition according to claim 1, wherein the copolymer of 2-acrylamido-2-methylpropanesulphonic acid and hydroxylated C$_2$-C$_4$ alkyl(meth)acrylate is salified in the form of a salt selected from alkali metal salts, ammonium salts, amino alcohol salts and amino acid salts.

6. The composition according to claim 1, wherein the copolymer of 2-acrylamido-2-methylpropanesulphonic acid and hydroxylated C$_2$-C$_4$ alkyl(meth)acrylate is salified in the form of the sodium salt.

7. The composition according to claim 1, wherein the copolymer of 2-acrylamido-2-methylpropanesulphonic acid and hydroxylated C$_2$-C$_4$ alkyl(meth)acrylate is present in an amount of from 0.1% to 10% by weight, relative to the total weight of the composition.

8. The composition according to claim 1, wherein it takes the form of an oil-in-water emulsion.

9. A method for non-therapeutic treatment of keratin materials, which comprises applying to said keratin materials a cosmetic composition as defined in claim 1.

10. The composition according to claim 2, wherein the compound of formula (I) is present in an amount of from 1% to 10% by weight, relative to the total weight of the composition.

11. The composition according to claim 3, wherein the compound of formula (I) is present in an amount of from 1% to 10% by weight, relative to the total weight of the composition.

12. The composition according to claim 1, wherein the compound of formula (I) is present in an amount of from 1.5% to 5% by weight, relative to the total weight of the composition.

13. The composition according to claim 2, wherein the copolymer of 2-acrylamido-2-methylpropanesulphonic acid and hydroxylated $C_1$-$C_4$ alkyl(meth)acrylate is salified in the form of a salt selected from alkali metal salts, ammonium salts, amino alcohol salts and amino acid salts.

14. The composition according to claim 3, wherein the copolymer of 2-acrylamido-2-methylpropanesulphonic acid and hydroxylated $C_2$-$C_4$ alkyl(meth)acrylate is salified in the form of a salt selected from alkali metal salts, ammonium salts, amino alcohol salts and amino acid salts.

15. The composition according to claim 4, wherein the copolymer of 2-acrylamido-2-methylpropanesulphonic acid and hydroxylated $C_2$-$C_4$ alkyl(meth)acrylate is salified in the form of a salt selected from alkali metal salts, ammonium salts, amino alcohol salts and amino acid salts.

16. The composition according to claim 2, wherein the copolymer of 2-acrylamido-2-methylpropanesulphonic acid and hydroxylated $C_2$-$C_4$ alkyl(meth)acrylate is salified in the form of the sodium salt.

17. The composition according to claim 3, wherein the copolymer of 2-acrylamido-2-methylpropanesulphonic acid and hydroxylated $C_2$-$C_4$ alkyl(meth)acrylate is salified in the form of the sodium salt.

18. The composition according to claim 4, wherein the copolymer of 2-acrylamido-2-methylpropanesulphonic acid and hydroxylated $C_2$-$C_4$ alkyl(meth)acrylate is salified in the form of the sodium salt.

19. The composition according to claim 1, wherein the copolymer of 2-acrylamido-2-methylpropanesulphonic acid and hydroxylated $C_2$-$C_4$ alkyl(meth)acrylate is present in an amount of from 0.5% to 5% by weight, relative to the total weight of the composition.

20. The composition according to claim 2, wherein the copolymer of 2-acrylamido-2-methylpropanesulphonic acid and hydroxylated $C_2$-$C_4$ alkyl(meth)acrylate is present in an amount of from 0.1% to 10% by weight, relative to the total weight of the composition.

* * * * *